United States Patent [19]

Leventhal

[11] 4,003,656
[45] * Jan. 18, 1977

[54] FINGERPRINT SCANNING DEVICE

[76] Inventor: Stephen Richard Leventhal, Suite 506E, 7315 Wisconsin Ave., Bethesda, Md. 20014

[ * ] Notice: The portion of the term of this patent subsequent to Feb. 4, 1992, has been disclaimed.

[22] Filed: Oct. 7, 1974

[21] Appl. No.: 512,862

Related U.S. Application Data

[63] Continuation-in-part of Ser. No. 359,008, May 10, 1973, Pat. No. 3,864,042.

[52] U.S. Cl. .......................... 356/71; 340/146.3 E; 356/167
[51] Int. Cl.² ........................................ G06K 9/08
[58] Field of Search ............ 250/571; 356/71, 167, 356/156

[56] References Cited

UNITED STATES PATENTS

| 1,756,232 | 4/1930 | Arnaud | 178/7.6 |
|---|---|---|---|
| 3,200,701 | 8/1965 | White | 356/165 |
| 3,511,571 | 5/1970 | Ogle | 356/156 X |
| 3,864,042 | 2/1975 | Leventhal | 356/71 |

FOREIGN PATENTS OR APPLICATIONS 1,172,539  12/1969  United Kingdom ............... 250/571

*Primary Examiner*—Robert Segal
*Attorney, Agent, or Firm*—Armstrong, Nikaido & Wegner

[57] ABSTRACT

A method and apparatus for rapidly scanning the finger of an individual with a monochromatic beam of light and for producing an output in accordance with the light reflected by the finger which corresponds to the fingerprint of the finger. The light beam is incident on the surface of the finger such that light incident upon the ridge of the finger is reflected along a predetermined path while light incident upon a trough of the finger is reflected along other paths. A detector is positioned in the predetermined path for detecting reflected light in that path. The detector therefore primarily detects light which is reflected from the ridge of the finger. The detected light is used to produce a signal indicative of the fingerprint of the finger.

7 Claims, 12 Drawing Figures

FINGERPRINT SCANNING DEVICE

RELATED APPLICATION

This application is a continuation-in-part of my copending application Ser. No. 359,008 filed May 10, 1973 now U.S. Pat. No. 3,864,042.

BACKGROUND OF THE INVENTION

1. Field of the Invention

This invention is related to a method and apparatus for producing a pattern corresponding to a fingerprint and more particularly to a method and apparatus for scanning a finger with a monochromatic light beam and for producing an output which corresponds to the ridges and troughs in the finger.

2. Description of the Prior Art

The use of fingerprints for determining the identity of an individual is a well-established technique of identification. Several prior art methods exist for producing an image which corresponds to the fingerprint. The most basic technique is the application of ink to the finger and then rolling the finger on a piece of paper. This produces an inked image which corresponds to the fingerprints. This technique has had several disadvantages. The four most obvious disadvantages are the fact the process is very messy because of the use of the ink and very slow because of the necessity of inking each finger and then rolling each finger onto the paper, lack of uniform quality between prints, and the rubber stamp effect distorting prints.

Another technique which has been used is to flood the surface of the finger with light which is then reflected by the surface. Due to the different reflective characteristics of the ridges and troughs, an image is produced which corresponds to the fingerprint. The reflected light may be passed through a transparency of a previously recorded fingerprint to produce an output which is indicative of the comparison of the fingerprint to the previously recorded fingerprint. This technique is disclosed in U.S. Pat. No. 3,511,571. The reflected light may also be scanned to produce an output indicative of the fingerprint. This technique is disclosed in U.S. Pat. No. 3,200,701. Systems using the technique of flooding the surface of the finger with light from a source do not have sufficient resolution to provide the required accuracy in many cases. This is due to the fact that the difference in reflected light from the ridges and troughs is relatively small. Furthermore, the signal derived from the reflected light is not amenable to automated data processing.

SUMMARY OF THE INVENTION

It is the primary object of this invention to provide a method and apparatus for producing an output indicative of the fingerprints of an individual.

It is another object of this invention to provide a method and apparatus for scanning a finger with a light beam and for producing an output corresponding to the ridges and troughs in the finger. This output is indicative of the fingerprint of the finger.

It is still another object of this invention to provide a rapid and inexpensive method and apparatus for producing facimiles of fingerprints and for storing or analyzing the fingerprint pattern.

This invention is for a method and apparatus for scanning a finger with a light beam and detecting the reflected light to produce an output which is indicative of the ridges and troughs on the finger and thereby the fingerprint. The finger is scanned in two directions such that the total surface area of the finger may be scanned. If a beam is incident upon a ridge of the finger, it is reflected along a predetermined path whereas if the beam is incident upon a trough in the finger, it is reflected along some other path. The predetermined path which is the path of a beam reflected by a ridge is predictable. Therefore a light detector placed in the predetermined path detects the ridges in the finger. An output device is connected to the light detector and produces a signal corresponding to the pattern of ridges and troughs on the surface of the finger.

DESCRIPTION OF THE PREFERRED EMBODIMENT

Figure 1:
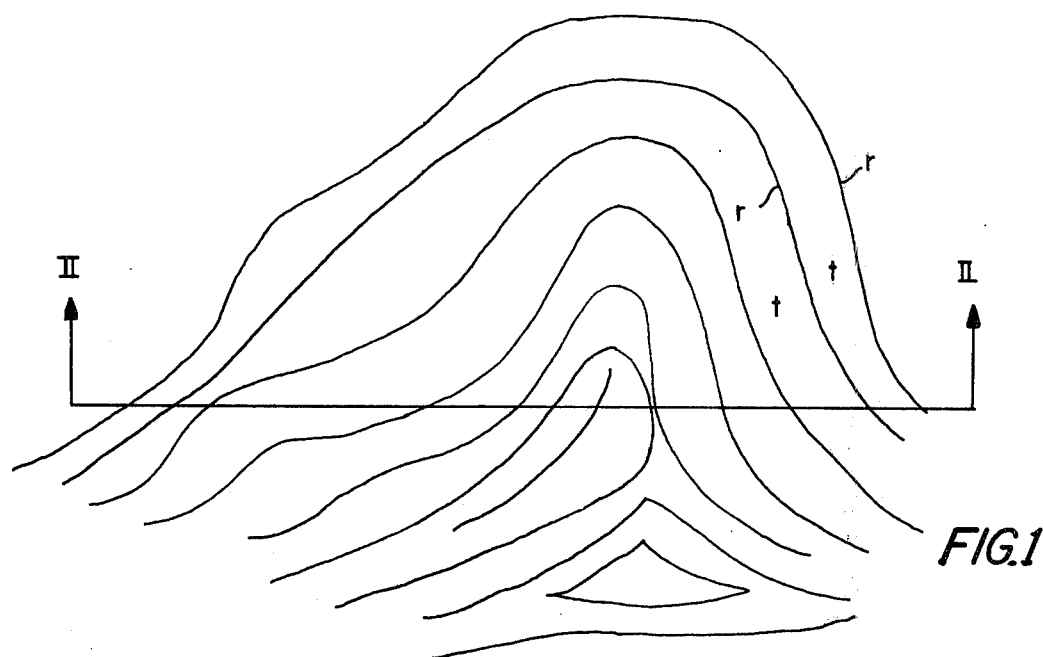
FIG. 1 is a ridge and trough pattern of a fingerprint.
Figure 2:
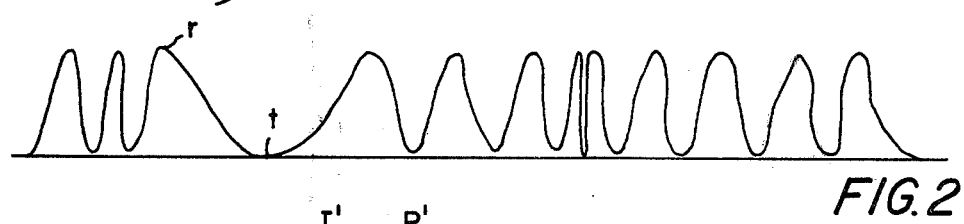
FIG. 2 is an elevation through section II—II in FIG. 1.

FIG. 1 illustrates a typical pattern of a surface of a finger having ridges R and troughs T. FIG. 2 is a section through II—II of FIG. 1 showing the relationship of the ridges and troughs. A trough between two ridges may be filled with air, grease, dirt or any other medium.

FIGS. 3–6 illustrate the principles of operation of the present invention.

Figure 3:
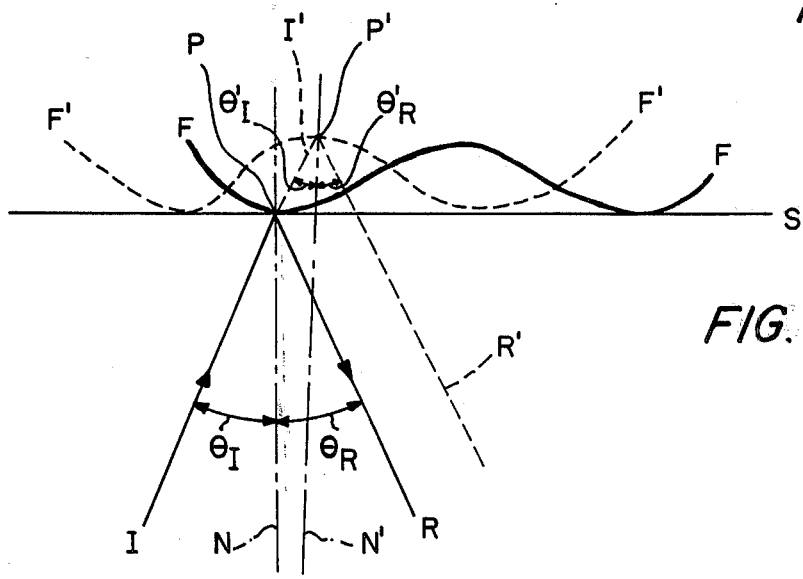
FIGS. 3–6 illustrate the principle of operation of the present invention.

Referring to FIG. 3, finger F is placed on a surface S which for now will be considered as having an infinitesimal thickness. A beam of light I is incident upon a finger F at point P. The beam is reflected along path R. Axis N is the normal to the surface of the finger F at point P. Notice that the angle of incidence $\theta_I$ equals the angle of reflection $\theta_R$. If the finger F is displaced as indicated by F' then the incident beam I after passing the point P continues to travel to point P' along path I'. At point P', the axis normal to the surface of the finger is N' which is not coincident and generally not parallel to N. The beam is then reflected along path R' where $\theta'_I$ equals $\theta'_R$. Note that the path R is different from the path R' both in direction and location.

The fact that the angle of incidence equals the angle of refraction in a reflected beam and that the angles are measured with respect to the normal to the surface from which the beam is reflected, is the basic principle upon which the present invention relies. The only beam which will follow a path R is a beam reflected from point P. Thus, if a detector is placed in the path R, the only beam that it will detect is that reflected from point P which is a ridge of the finger. A beam along path R' from the trough will not be detected by the detector.

Figure 4:
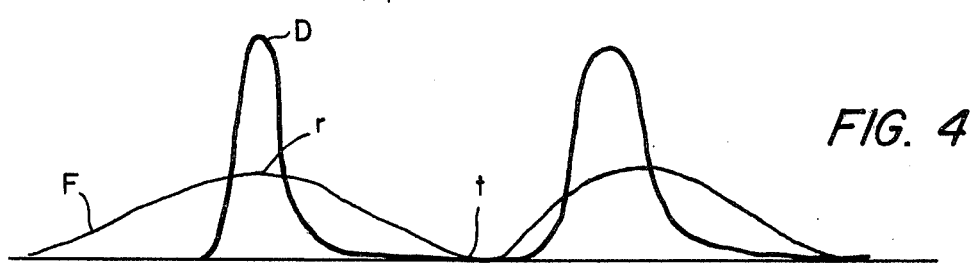

FIG. 4 shows the relationship between the detected signal D and the surface of the finger F. Peaks of detected signal D are very sharp having a magnitude very high with respect to the reference level whereas the height between ridges and troughs is relatively small and the transition is very smooth. It can be seen therefore that by taking advantage of the principles illustrated in FIG. 3 that a signal corresponding to the fingerprint can be derived which has excellent resolution and may be easily interpreted because of the distinct difference in signals produced by ridges and troughs of a fingerprint.

Figure 5:
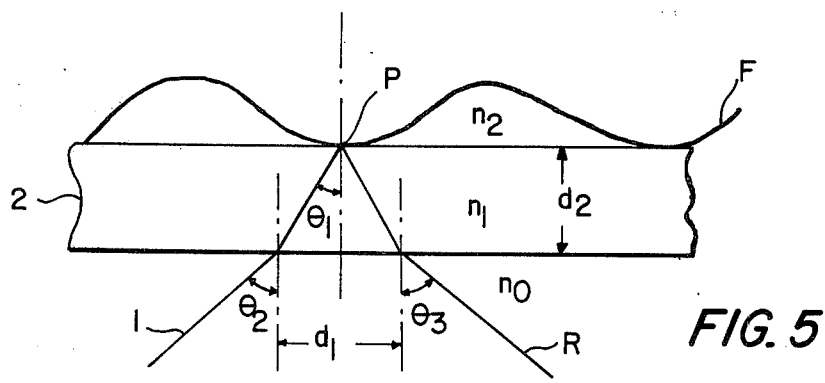

FIG. 5 illustrates the principle of operation of the invention taking into consideration the thickness of a plate 2 having parallel faces upon which the finger F is placed when a fingerprint is being read. The area below plate 2 has an index of refraction $n_o$, the plate and index refraction $n_1$ and the trough of the finger an index of refraction $n_2$. An incident beam I follows the path shown to point P where it is reflected along a path R. Using Snell's Law, $\theta = \text{Sin}^{-1} (n_o/n_1 \text{ Sin } \theta_2)$ and $d_1 = 2d_2 \tan \theta_1$. Since $\theta_2$, $n_o$, $n_1$, and $d_2$ are all known, $\theta_1$ and thereby $d_1$ can be determined. Further, since $\theta_2$ equals $\theta_3$, the path of the reflected light R can be determined and a detector can be placed in that path.

Figure 6:
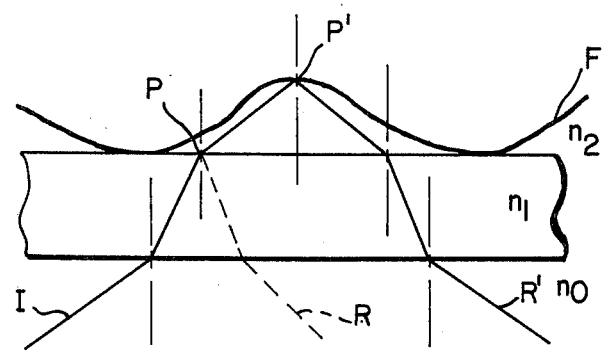

FIG. 6 is similar to FIG. 5 except that the relationship between the incident beam I in the finger F is such that the incident beam I follows a path which is reflected off of point P' in the trough of the finger F. The reflected beam follows a path R', the dotted line R illustrates the path that a reflected beam would have followed had it been reflected off of a ridge at point P. Although it is possible for some points P' that paths R and R' may intersect, they will never be coincident. It is evident that if a detector were placed in path R as described with respect to FIG. 5, the reflected beam R' in FIG. 6 would not be detected, thus indicating a trough.

Figure 7:
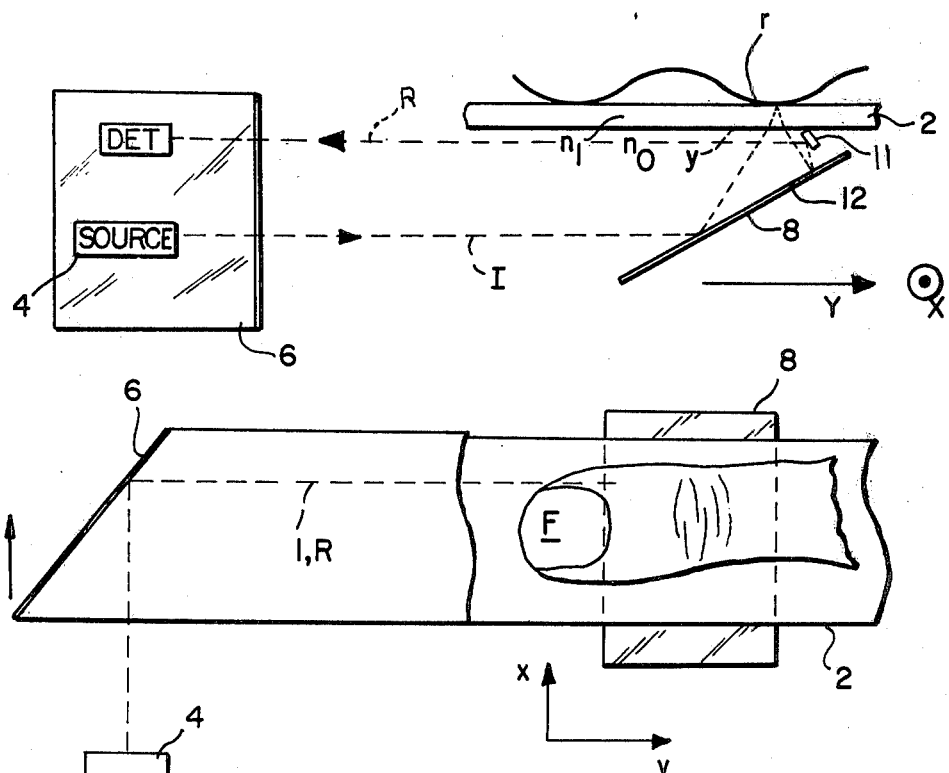
FIG. 7 is a side view of the apparatus of preferred embodiment.
Figure 8:
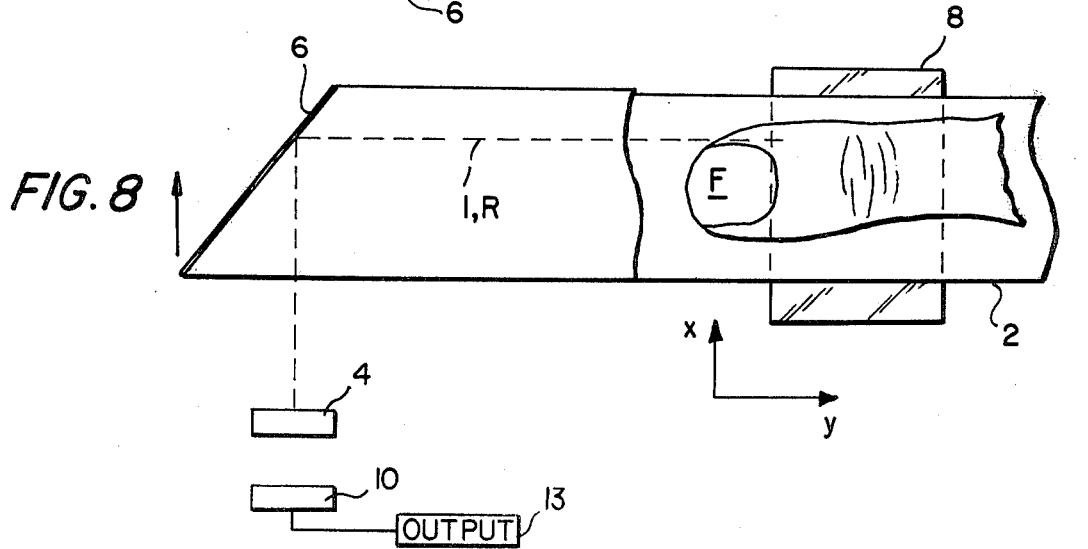
FIG. 8 is a plan view of the apparatus of the present invention.

FIGS. 7 and 8 illustrate a side and plan view of the apparatus of the preferred embodiment of the invention. A source of monochromatic light 4, such as a laser, projects light along a path I which is reflected off of a surface 6 then off of surface 8 up to plate 2 where the beam is bent due to the difference in index of refraction of the plate 2. The beam is then reflected by finger F and follows a path R back to detector 10. If the beam I were reflected by the trough of the finger F, the reflected beam would not follow the path R and thus would not be detected by the directional detector 10. The directional detector 10 can be positioned to detect only beams reflected by a ridge R of the finger F, since point 12 and the position of mirror 11 can be determined by the principles illustrated in FIG. 5.

In order to get a complete picture of the fingerprint, it is necessary to scan the surface of the finger with the beam of light from source 4. The scanning in the X direction is done by means of reflector 6 while the scanning in the Y direction is done by means of reflectors 8 and 11. If reflecting surface 6 is a reciprocating mirror, it can be seen that as the surface moves in the X direction, the beam I is moved laterally in the X direction. Reflecting surfaces 8 and 11 are reciprocating surfaces which move together in the Y direction. If the incident beam is horizontal, then as reflectors 8 and 11 move in the Y direction, the point y also moves in the Y direction and thus the point of reflection off of the surface of finger F moves in the Y direction. By coordinating the movement of reflecting surface 6 and reflecting surfaces 8 and 11, the surface of finger F can be rapidly scanned to produce an output, in output device 13, indicative of the fingerprint. The output device 13 could be a recorder, display device, or any other device for receiving a signal which has a pattern indication of the finger.

Figure 9:
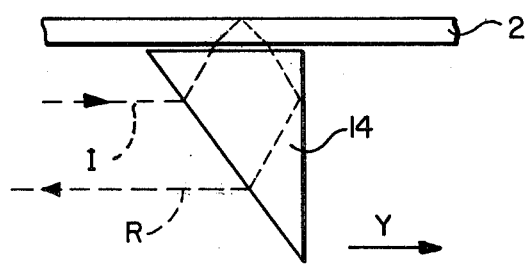
FIG. 9 is an alternate embodiment of the scanning mechanism of the present invention.

In the embodiment shown in FIGS. 7 and 8, reflecting surfaces 8 and 11 are illustrated as a mirror. However, as shown in FIG. 9, a prism can be used and the light travels the path illustrated. The prism is moved in a reciprocating manner along axis Y.

Reflecting surface 6 may also be any number of different types of reflecting surfaces rather than the reciprocating plane mirror shown in the preferred embodiment. Specifically, the surface 6 could be a rotating or reciprocating prism, or a rotating mirror.

The surface of a rotating reflector, either a mirror or prism, is designed so that as the reflector rotates, the orientation of the reflected ray is at all times parallel to the prior position. Therefore, the surface is designed so that the angle of incidence of the beam with the reflecting surface is always constant as the reflector rotates.

Figure 10:
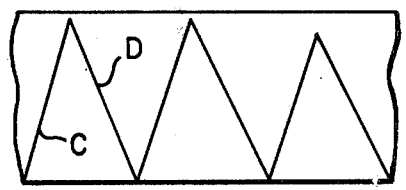
FIGS. 10–12 illustrate scanning patterns of the scanning mechanism of the present invention.
Figure 11:
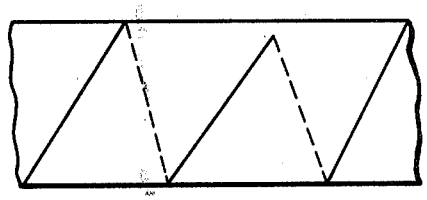
Figure 12:
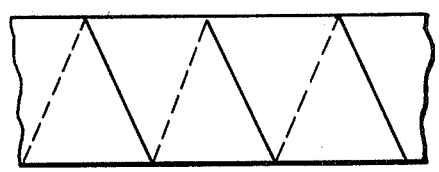

FIGS. 10 through 12 illustrate scan patterns which will be traced on the surface of a finger. FIG. 10 is the basic scan pattern which is traced when the beam from source 4 is reflected in the manner described above by reflecting surfaces 6, 8 and 11. If a scan pattern such as that shown in FIG. 11 is desired, a blanking signal may be used to cut off the source 4 or to block the detector 10 during portion D of the scan shown in FIG. 10. FIG. 12 illustrates a scan pattern which was developed when blanking is used during portion C of the scan pattern of FIG. 10.

Although in the preferred embodiment, a stationary source and detector are used with a movable reflector, a movable source and detector could be used with stationary reflectors or with moving reflectors.

Because of the large magnitude of the difference between signals reflected by ridges as opposed to troughs and sharp peaks produced by the presence or absence of reflected light, corresponding respectively to a ridge or trough in a finger, the output of detector 10 is extremely useful.

The method and apparatus described, rapidly and inexpensively produces images of fingerprints, sortes them for display, transmission or comparison with previously recorded prints. Due to the scanning of the finger with a laser, resolution in the order of 1/1000'' is obtainable.

While the invention has been particularly shown and described in reference to the preferred embodiment of the above, it will be understood by those skilled in the art that various changes and details may be made therein without departing from the scope and spirit of the invention.

I claim:
1. A system for producing a pattern comprising ridges and troughs in accordance with a fingerprint of an individual's finger, said system comprising:
 a. light source means;
 b. scanner means for scanning said light source over said finger in a point-by-point scan, said scanner means comprising first means including a reflector means for scanning said light source along one axis of said finger; second means positioned to receive the light from said first means, for directing the light to said finger along a path such that said light is reflected by said finger and for directing the light reflected by a ridge in said finger along a predetermined path, wherein the light reflected by a trough is directed along other paths, and driver means for driving said second means such that the light source is scanned along a second axis of said finger;
 c. detector means for detecting only the light from said light source means reflected along said predetermined path by said finger; and wherein said second means includes first and second mirrors positioned such that light from said first means is reflected by said first mirror towards said finger and light reflected by a ridge along said predetermined path is then reflected by said first mirror towards said second mirror and said light is then reflected by said second mirror such that it is detected by said detector means; and e. output means, coupled to said detector means, for reproducing said pattern of ridges and troughs in accordance with the light detected by said detector means, wherein said pattern corresponds to the fingerprint of said finger.

2. The system of claim 1 wherein said light source is monochromatic.

3. The system of claim 2 wherein said light source is a laser.

4. The system of claim 1 wherein said first and second means are rotatable mirror means.

5. The system of claim 1 wherein said first and second means are reciprocating mirror means.

6. The system of claim 1 wherein said first means is a rotatable mirror means and said second means is a reciprocating mirror means.

7. The system of claim 1 wherein said output means includes recorder means for recording said output signal.

* * * * *